United States Patent [19]

Marcel

[11] Patent Number: 4,992,475

[45] Date of Patent: Feb. 12, 1991

[54] BUTYLHYDROXYANISOLES FOR THE TREATMENT OF RETROVIRAL DISEASES

[75] Inventor: Georges Marcel, Paris, France

[73] Assignee: Roussel Uclaf, Paris, France

[21] Appl. No.: 297,254

[22] PCT Filed: Apr. 8, 1988

[86] PCT No.: PCT/FR88/00173

§ 371 Date: Dec. 5, 1988

§ 102(e) Date: Dec. 5, 1988

[87] PCT Pub. No.: WO88/07856

PCT Pub. Date: Oct. 20, 1988

[30] Foreign Application Priority Data

Apr. 10, 1987 [FR] France ................................ 87-05088

[51] Int. Cl.$^5$ ............................................ A61K 31/075
[52] U.S. Cl. .................................................... 514/718
[58] Field of Search .......................................... 514/718

[56] References Cited

PUBLICATIONS

Chemical Abstracts, 85:87941j (1976).
Reimund, The Lancet, Nov. 15, 1986, p. 1159.

Primary Examiner—Jerome D. Goldberg
Attorney, Agent, or Firm—Bierman and Muserlian

[57] ABSTRACT

The invention concerns chemical compounds consisting of the buty hydroxyanisoles and their salts for use in a method of therapeutic treatment of the human or animal body, in particular for use in a method of prophylactic or curative treatment of retroviral diseases, such as AIDS.

4 Claims, No Drawings

BUTYLHYDROXYANISOLES FOR THE TREATMENT OF RETROVIRAL DISEASES

The present invention relates to the chemical compounds consisting of butylhydroxyanisoles and their salts as agents suitable for the therapeutic treatment of the human or animal body. The compounds of the invention, designated compounds (I), comprise, in particular, tert-butylhydroxyanisoles such as 3-tert-butyl-4-hydroxyanisole (II), 2-tert-butyl-4-hydroxyanisole (III) and the mixture (IV) in variable proportions of these 2 products, this mixture sometimes being designated by the term B.H.A.

The subject of the invention is, in particular, the use of the compounds (I) for the treatment of diseases caused by retroviruses, for example for the treatment of AIDS.

The compounds of the invention and their salts, such as the alkali metal salts, are chemical compounds which have been known for a long time. The compounds (II) and (III) and a mixture thereof, in particular the compound (IV) known as B.H.A., possess very advantageous antioxidant properties, while having as little toxicity as possible towards man and animal. In particular, these studies have shown the absence of harmful effects of oral doses ranging, in rhesus monkeys up to 500 mg/kg/d for 1 month, in cynomolgus monkeys up to 400 mg/kg/d for 3 months, in pigs up to 400 mg/kg/d for 4 months, and in beagle dogs up to 220 mg/kg/d for 6 months. For this reason, they are widely used, such as B.H.A., as food additives for the preservation of edible fats and oils and of many other foods for human consumption. They are also used as preservatives in the manufacture of medicinal compounds. However, it appears that these compounds have never been used as active principles for a therapeutic purpose as regards man or animals.

It is known, moreover, that retroviruses, to which the AIDS virus (H.I.V. or H.T.L.V. III or L.A.V.) belongs, are enveloped viruses. Now, according to current knowledge, it would appear that the AIDS virus is pathogenic as the result of a 2-stage mechanism:

in a first stage, the envelope of the retrovirus adheres to a membrane receptor of cells such as T4 lymphocytes.

In a second stage, the retrovirus enters the cell and, as a result of the reverse transcriptase, its RNA is transcribed to DNA, which is integrated in the genome of the infected cell which, in consequence, is capable of providing for the multiplication of the virus.

Hitherto, therapeutic investigations relating to AIDS have been chiefly concerned with the second stage of the mechanism described above, use being made, in particular, of inhibitors of reverse transcriptase or of other enzymes involved in the replication, transcription and translation of nucleic acids.

It does not appear, on the other hand, that the first stage of the supposed mechanism of action of the AIDS retrovirus has hitherto given rise to detailed studies. Specifically in an in endeavor to develop a therapy for AIDS, the author of the present invention directed his attention towards the first stage of this mechanism, that is to say towards the adhesion of the viral envelope to the cell receptor, its mechanism, its biochemical substrate and the means of modifying it. The importance of this envelope is borne out by the size of the corresponding transcription unit (or gene, or "open reading frame"=orf). In effect, H.I.V. possesses at least 6 orfs: the bulkiest (or "pol") codes for reverse transcriptase, and the next bulkiest (or "env") codes for a precursor glycoprotein (g Pr 160) which is cleaved to an external glycoprotein (gp 120) and a transmembrane glycoprotein (gp 41), of unusual sizes.

It was then shown, and this forms the main subject of the present invention, that the compounds (I) as defined above, show exceptional and surprising properties, having the effect of abolishing, reducing or modifying the infectivity of the AIDS virus. This effect is very probably due to an alteration of the envelope of this retrovirus and, on this assumption, could hence intervene in the first stage of the mechanism stated above.

A related effect has, admittedly, been envisaged recently for 2,6-di-tert-butyl-4-methylphenol, or B.H.T.; this concerned, however, only a working hypothesis. Moreover, the studies conducted previously on B.H.A. and B.H.T., more especially on the latter compound, related to viruses not belonging to the category of retroviruses, and suggested, first and foremost, potential uses. Subsequently, the application of B.H.T. to the prophylaxis of Newcastle disease of chickens and to the curative treatment of herpes was tested but proved very disappointing (see Snipes, Person, Keith, Cupp Science (1975), 187, 64; Wanda, Cupp, Snipes et coll. Antimicrobial Agents and Chemotherapy (1976), vol. 10, page 96; Brugh M. Science. (1977), vol. 197 pages 1291-1292; Freeman D. F., Wenerstrom G., Spruance S.L. Clin. Pharmacol. Therap. (1985), vol. 38, pages 56-59).

The subject of the present invention is hence the use of the compounds (I) as antiviral and/or anti-infective or antiseptic agents.

The antiviral activity of the compounds (I) of the invention, in particular of the compound (II), was demonstrated on H.I.V. viruses originating from a culture supernatant of cells that are continuously productive of this virus. It is illustrated later in the experimental part.

By virtue of their antiviral and/or anti-infective properties, as well as their acknowledged safety with respect to man, the compounds (I) according to the invention find their use as medicinal products, for example, in the treatment of retroviral diseases, in particular AIDS. For a therapeutic use of this kind, pharmaceutical compositions, which are also the subject of the invention, containing as active principle a compound (I) such as the compound (II) or a mixture of compounds (I) and a pharmaceutically inert excipient, are prepared according to the usual methods.

Among the usual pharmaceutical forms that are suitable for providing the best prophylactic treatment, there may be mentioned creams, ointments, gels, lotions, powders, emulsions and aerosols. Among the latter, genital aerosols, oral aerosols and vaginal gels with an applicator are most especially recommended. The excipient used in these compositions will preferably be a viscous excipient enabling the active principle to persist at potential sites of inoculation.

Among such excipients, there may be mentioned:

(A) neutral oils of the type comprising triglycerides of $C_8$-$C_{12}$ saturated fatty acids of plant origin, with or without $Ca^{++}$ ions (B) 90-97% strength ethanol containing 0.10 to 0.20% of cellulose esters, with or without $Ca^{++}$ ions.

The dose of compounds (I) in these compositions can depend on the form used. It will be, in particular, between 0.01% and 1% of active principle, and preferably of the order of 0.02%. The maximum daily dose of active principle, which varies according to the subject to be treated, is of the order of 30 mg, which can correspond, for example, for an oral aerosol to about 30 sprayings.

Also in the context of the present invention, by virtue of the capacity of the compounds (I), such as the compounds (II) and (IV), to inactivate completely the infectious power of the HIV 1 virus, and in view of the safety and ease of handling of these molecules, borne out by toxicological and pharmacokinetics studies, the compounds (I) of the invention, in particular the compound (II), must have their place in the treatment of infections caused by the HIV 1 virus and related viruses. This therapeutic use may be applied to simple seropositivity, to the syndrome known as ARC (AIDS-related complex) or to the AIDS disease. In a curative treatment of this kind, the compound (II), in particular, may be administered orally or parenterally, especially via the slow intravenous route.

The dosage can vary according to the administration route, the condition treated and the subject in question. For example, it will vary between 50 and 100 mg/kg/day orally and between 1 to 10 mg/kg/day parenterally.

The compounds of the invention, such as (II), may be employed alone or mixed, or alternatively even in combination with other medicinal products presented for the treatment of AIDS, such medicinal products not acting on the same infectious phenomenon as the compounds (I).

Among possible combinations, there may be mentioned, for example, the combination with azidothymidine, dideoxycytidine, HPA-23 and AL-721.

The subject of the present invention is hence also the use of the compounds (I) for the manufacture of medicinal products intended for the treatment of retroviral diseases such as AIDS, as well as for the manufacture of medicinal products having an antiviral and/or anti-infective activity against the AIDS virus and related viruses.

The property, demonstrated for the compounds (I), of acting on the infectivity of the virus responsible for AIDS enables, moreover, the compounds of the invention, in particular the compounds (II) and (IV), to be used for the preparation of anti-AIDS vaccines according to the usual methods for preparing vaccines. In this use, which is also a subject of the present invention, the compounds (I) act as agents that modify the infectivity of the AIDS retrovirus while not destroying its physical and antigenic characteristics. As a result of this action, they enable a retrovirus to be prepared having attenuated infectivity but sustained antigenicity, thus being capable of being the source of a vaccine.

Likewise, in the light of the properties of the compounds (I), in particular their anti-infective and/or antiseptic properties, the subject of the invention is also these compounds as anti-infective and/or antiseptic products, as well as the compositions containing these products. These compositions are intended for locally combating retroviruses such as the AIDS virus by abolishing or reducing their infectivity. Such compositions, intended for human use, in view of their form and purpose, would not be or might not be regarded as pharmaceutical compositions. Among possible forms of use, there may be mentioned, in particular, chewing gums, lip salves, soaps, milks, shower gels and mouth washes. These compounds are prepared according to the usual methods.

These anti-infective and/or antiseptic products, as defined above, and compositions containing them, are also suitable for use applied to articles or in premises likely to be infected with the AIDS virus.

Among the compositions possible for a use of this kind, there may be mentioned aerosols, waxes and coatings.

The examples which follow illustrate the invention without, however, limiting the latter.

EXAMPLE 1

A stock solution of 3-tert-butyl-4-hydroxyanisole (II) at a concentration of 0.5 M in 95% strength ethanol was prepared, and its compatibility tested with RPMI 1640 culture medium to which fetal calf serum (10%), interleukin-II (10%) and anti-human interferon serum have been added.

It is verified that concentrations of $10^{-5}$ to $10^{-3}$ M of compound (II) are not toxic for T lymphocytes, directly and after washing.

H.I.V. viruses (originating from a supernatant of cells that are continuously productive of H.I.V. virus, of reverse transcriptase activity titer greater than $10^5$ cpm/ml) incubated for 5, 10, 30 or 60 minutes at 37° with concentrations of $10^{-5}$ to $10^{-3}$ M of compound (II) are then brought into contact with T lymphocytes of a normal donor (stimulated with PHA-P for 3 days, and then cultured in medium to which IL-II and anti-human interferon serum have been added). The infectivity of these preparations is determined by following the viral production (reverse transcriptase activity) in the culture supernatants of infected T cells, at each cell passage (every 3 or 4 days) for one month.

The infectivity of the H.I.V. viruses is maintained in untreated controls or controls treated with $10^{-5}$ or $10^{-4}$ M concentrations of compound (II). It disappears when the compound (II) is used at a final concentration of $10^{-3}$ M.

Thus, at this concentration, a minimum incubation, of 30 minutes, shielded from the light and at a temperature of 37° C., of the compound (II) with the HIV 1 virus suffices to inactivate completely the infectious power of the AIDS virus.

A comparative study performed with 2,6-di-tert-butyl-4-methylphenol or B.H.T. gives the following result at D+4:

| | |
|---|---|
| Compound (II): | 355 |
| B.H.T.: | 113,624 |

(the FIGURES represent the reverse transcriptase activity, that is to say the viral production, expressed in c.p.m./ml). It also shows that the anti-AIDS activity is not present in a closely related derivative.

EXAMPLE 2

GENITAL AEROSOL

The genital aerosol consists of a $10^{-3}$ M solution of compound (II) in an excipient of the type (A) or (B).

This viscous solution is designed to enable the genital regions likely to be contaminated to be covered. One spraying will correspond to 5 ml, equivalent to 0.9 mg of active principle, thereby permitting 30 sprayings per day without exceeding the maximum dose accepted for the oral route.

EXAMPLE 3

ORAL AEROSOL

The oral aerosol consists of a $10^{-3}$ M mentholated solution of compound (II) in an excipient of the type (A) or (B).

This viscous solution is designed to enable the endobuccal mucosa to be covered. One spraying will also correspond to 5 ml, equivalent to 0.9 mg of active principle.

EXAMPLE 4

VAGINAL GEL WITH APPLICATOR

The vaginal gel consists of a $10^{-3}$ M gel of compound (II), designed to enable the vaginal mucosa to be covered. The unit dose is 5 ml, equivalent to 0.9 mg of active principle.

What is claimed is:

1. A method of treating retroviral diseases in warm-blooded animals comprising orally or parentally administering to warm-blooded animals in need thereof an amount of at least one compound selected from the group consisting of 3-tert.-butyl-4-hydroxy-anisole and 2-tert.-butyl-4-hydroxyanisole and their non-toxic, pharmaceutically acceptable salts sufficient to treat retroviral infections.

2. The method of claim 1 wherein the active compound is 3-tert-butyl-4-hydroxy-anisole.

3. The method of claim 1 wherein the active compound is a mixture of 3-tert.-butyl-4-hydroxy-anisole and 2-tert.-butyl-4-hydroxy-anisole.

4. The method of claim 1 wherein the retroviral disease is Aids.

* * * * *